United States Patent [19]

White, Jr.

[11] 4,327,734

[45] May 4, 1982

[54] THERAPEUTIC METHOD OF USE FOR MINIATURE DETACHABLE BALLOON CATHETER

[76] Inventor: Robert I. White, Jr., 2615 Pot Spring Rd., Timonium, Md. 21093

[21] Appl. No.: 191,415

[22] Filed: Sep. 29, 1980

Related U.S. Application Data

[63] Continuation of Ser. No. 6,028, Jan. 24, 1979, abandoned.

[51] Int. Cl.³ ............................................ A61B 17/12
[52] U.S. Cl. ................................................... 128/325
[58] Field of Search ........ 128/1 R, 325, 344, 348–351

[56] References Cited

U.S. PATENT DOCUMENTS

| | | | |
|---|---|---|---|
| 3,834,394 | 9/1974 | Hunter et al. | 128/325 |
| 4,029,104 | 6/1977 | Kerber | 128/349 B |
| 4,085,757 | 4/1978 | Pevsner | 128/325 |
| 4,157,085 | 6/1979 | Austad | 128/1 R |

OTHER PUBLICATIONS

*Radiology,* vol. 126, No. 2, pp. 521–523, Feb. 1978, White et al.
*Am. J. Roentgenol,* 128: 225–230, Feb. 1977, Pevsner.

*Primary Examiner*—C. Fred Rosenbaum
*Attorney, Agent, or Firm*—Kane, Dalsimer, Kane, Sullivan and Kurucz

[57] ABSTRACT

A therapeutic medical procedure utilizing a miniature balloon catheter of the type including a resilient cannula adapted for attachment to a source of fluid in having a small outer diameter for insertion into small vessels containing fluid and an inflatable balloon having a mouth at the proximal end thereof. The balloon is attachably mounted on the end of the cannula in fluid communication therewith and the balloon is designed to seal when the cannula is attached therefrom. The medical technique includes inserting the balloon catheter into a small vessel and permitting the catheter to advance to a desired location in the vessel. The balloon catheter is attached to a source of fluid having an osmolarity substantially the same as the fluid in the vessel and the balloon is inflated to the volume limits of the balloon with fluid from the fluid source through the cannula until the balloon is fixed in position in the vessel. The cannula is then detached from the balloon and removed from the vessel. The mouth of the inflated balloon is self-sealed with the fluid from the fluid source therein to maintain the balloon in inflated position for an extended period of time thereby creating a vessel occlusion.

31 Claims, 6 Drawing Figures

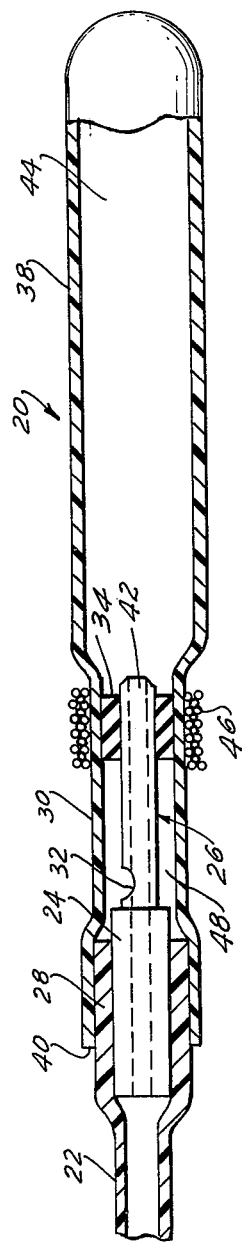
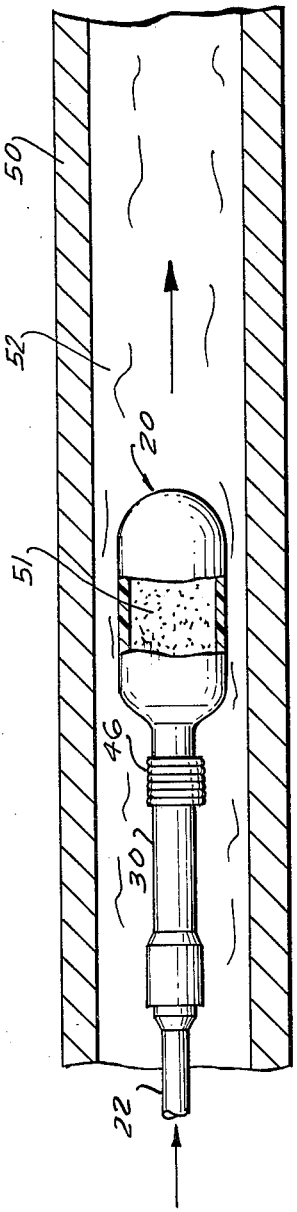
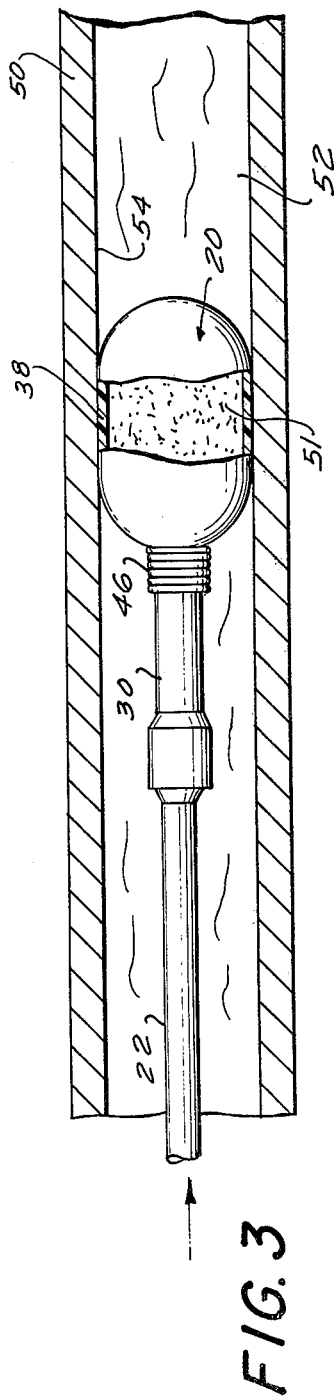
FIG.1
FIG.2
FIG.3

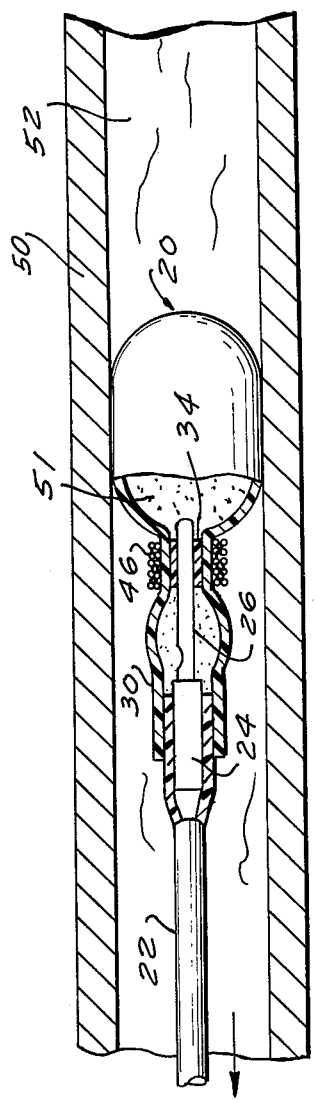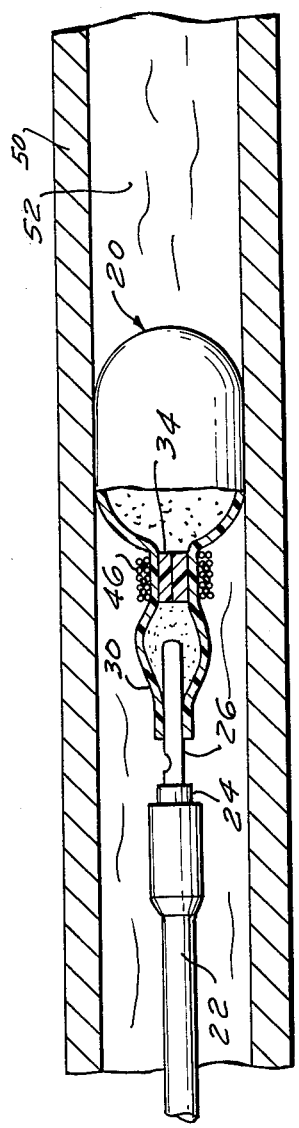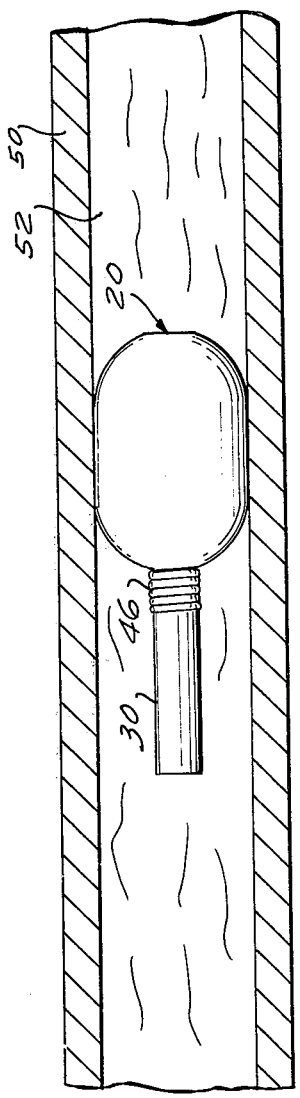

THERAPEUTIC METHOD OF USE FOR MINIATURE DETACHABLE BALLOON CATHETER

This is a continuation, of application Ser. No. 6,028, filed Jan. 24, 1979 and now abandoned.

BACKGROUND OF THE INVENTION

The development of miniature balloon catheters for use in small tortuous locations such as neurological blood vessels is an extremely active and dynamic field. The development can be traced through the work of Dr. Serbineko of Russia as published in the Journal of Neurosurgery, Volume 41, August 1974, pages 125–145 and entitled Balloon Catherization and Occlusion of Major Cerebral Vessels. An example of more recent work in the area is present in U.S. Pat. No. 4,085,757 issued to Dr. Paul H. Pevsner on Apr. 25, 1978.

The rapid development of the art is readily apparent and the visible field of use becomes greater as experimental work continues within the medical profession. A variety of improved designs for miniature balloon catheters for detachment, perfusion and other purposes are being developed at rapid rate with improvements being conceived constantly. Naturally proceeding hand-in-hand with the improved devices is a sequence of improved techniques in the use of balloon catheters both for neurological purposes and for use in other body vessels and cavities.

Original developments is the use of detachable perfusion balloons were primarily directed toward the diagnosis and treatment of neurological diseases. In certain instances larger non-detachable balloons have been utilized for emergency preoperative control of hemorrhage in the abdominal circulation, but most efforts have centered about therapeutic embolization with a variety of materials.

One particular area open for development is in the use of the detachable balloon occlusion as offering a method for precise and possibly long-term occlusion without the dangers of inadvertent embolization associated with the injection of particulate matter through a catheter. There is very little data available describing the possible variables influencing balloon occlusion.

SUMMARY OF THE INVENTION

With the above background in mind, it is among the primary objectives of the present invention to present a technique for use of detachable balloons for therapeutic embolization. The objective is accomplished by the consideration of the osmolarity of radiopaque media used to fill the balloon. A description of the development of the present invention appears in Radiology, Volume 126, No. 2, pages 521–523, published in February 1978 and entitled Therapeutic Embolization With Detachable Balloons. The content of that publication pertaining to the present invention is incorporated herein by reference.

As pointed out in the above publication dealing with the subject matter of the present invention, osmolarity of the distending contrast media is an important variable influencing the permanency of balloon occlusion, particularly where the balloon is of a semi-permeable material such as a silicone membrane commonly known as Silastic rubber. Silastic is a trademark of Dow Corning Corporation. It is an objective to use a fluid to produce the desired conditions for long term embolizations.

In utilizing a semi-permeable membrane material such as a silicone material for the expandable balloon, for example a Silastic rubber balloon, the following compounds have been found effective to produce the desired osmolality conditions particularly for radiopaque contrast media. A first is R-60 manufactured by Squibb, Inc., Princeton, N.J. 08540 containing 60% Nameglamine diatrizoate diluted to a 30 percent iodine concentration and identified as R-30. A second is metrizamide, a non-ionic, fluid contrast medium manufactured by Sterling-Winthrop Research Institute of Rensselaer, N.Y. 12144. A third is Iodipamide Meglumine manufactured by Squibb, Inc., Princeton, N.J. 08540 currently available for introvascular use and nearly iso-osmotic when diluted by 30% with sterile water.

It is contemplated that in dealing with a silicone balloon as the detachable member, it acts as a semi-permeable membrane and permanency of the detached balloon inflation is dependent on the osmolarity of the filling substance within the volume limits of the detachable balloon.

In order to prevent premature or undue swelling and rupturing as well as loss of radiopacacity of the balloon implant, a radiopaque filler of similar osmolarity to blood is used. As a result, the longevity of the balloon is increased and a more effective and better therapeutic embolization is achieved.

In summary, a therapeutic medical procedure is provided utilizing a miniature balloon catheter of the type including a resilient cannula adapted for attachment to a source of fluid and having a small outer diameter for insertion into small vessels containing fluid. An inflatable balloon having a mouth at the proximal end thereof is detachably mounted on the end of the cannula in fluid communication therewith. Sealing means is on the catheter to close the mouth of the balloon when the cannula is detached therefrom. The procedure involves inserting the balloon catheter into a small vessel. The catheter is advanced in the vessel to the desired location. The balloon catheter is attached to a source of fluid having an osmolarity substantially the same as the fluid in the vessel and the balloon is inflated with the fluid from the fluid source traveling through the cannula until the balloon is fixed in position in the vessel. The cannula is then detached from the balloon and removed from the vessel. The sealing means seals the mouth of the inflated balloon with the fluid therein to maintain the balloon in inflated position for an extended period of time to create a vessel occlusion.

With the above objectives among others in mind, reference is made to the attached drawings.

BRIEF DESCRIPTION OF THE DRAWINGS

In The Drawings:

FIG. 1 is a fragmentary sectional view of the catheter utilized in performing the medical procedure of the invention;

FIG. 2 is a fragmentary sectional view of the catheter inserted into a small vessel and partially expanded by introduction of fluid so that the catheter is floated along with the liquid in the vessel to the desired location;

FIG. 3 is a fragmentary sectional view thereof with the balloon having been expanded to seal against the walls of the vessel;

FIG. 4 is a fragmentary sectional view thereof with fluid being introduced to detach the balloon from the cannula;

FIG. 5 is a fragmentary sectional view thereof with the cannula detached from the balloon and being removed therefrom and the balloon sealed;

FIG. 6 is a fragmentary sectional view thereof with the cannula having been removed from the balloon and the balloon being retained in sealed expanded position in the vessel with fluid therein to create a vessel occlusion.

DETAILED DESCRIPTION OF THE PREFERRED EMBODIMENTS

The miniature balloon catheter assembly 20 adaptable for use in the medical technique of the present invention as shown in the drawings is essentially described in detail in copending application Ser. No. 717,746, filed on Aug. 25, 1976. It includes a hollow cannula 22 of polyurethane material or any conventional substitute therefor. One end of cannula 22 is adapted to be connected to a source of fluid in a conventional manner. Mounted in the other end of cannula 22 is an enlarged end 24 of a pin 26. The enlarged end 24 expands the end portion 28 of the cannula so that a frictional fit is presented therebetween. The pin has a passageway 30 therethrough and a side opening 32 adjacent the wider diameter portion 24. The smaller end of the pin 30 is positioned within a self-sealing plug 34 mounted in the open end portion 36 of an expandable balloon 38. The balloon 38 can be formed of a conventional material such as a semi-permeable membrane of silicone commonly known as Silastic rubber. The end portion 36 of balloon 38 terminates in an open mouth 40. The mouth 40 is expanded to frictionally seat on the outer surface of expanded end portion 28 of cannula 22. The end of pin 30 extends through plug 34 so that the opening 42 at its forward end is in communication with the hollow interior 44 of the balloon 38. The passageway 30 through the pin 26 communicates with the hollow interior of cannula 22 and with the interior of balloon 44 thereby providing a passageway for fluid into the balloon.

Surrounding the portion of the balloon where the plug 34 is located on the exterior surface thereof is an elastic band 46 of plastic or rubber material which assists in retaining the pin in the self-sealing plug and is utilized to assist with the self-sealing plug in sealing the open end of the balloon when the cannula and pin combination is removed therefrom during detachment. A secondary small chamber 48 between the end of the cannula 22 and the self-sealing plug 34 communicates with side opening 32 and provides the area for additional fluid utilized to expand end portion 36 of the balloon and facilitate withdrawal of the cannula and pin therefrom during detachment.

The self-sealing plug 34 can be formed of any commonly used self-sealing plastic or natural or synthetic rubber material. Similarly, the pin 26 can be formed of a rigid plastic or a metal substitute therefor.

In the steps of use, the catheter 20 is introduced to the vessel in the same manner as in the above referenced copending application. An introductory catheter is inserted through the body into the vessel to provide a passageway for catheter 20 and then the catheter is passed through the introducing catheter until it is positioned within the vessel 50 as shown in FIG. 2. The vessel 50 is filled with a fluid such as blood 52 traveling in the direction shown by the arrow in FIG. 2. Radiopaque contrast media in the form of a fluid having an osmolarity substantially the same as blood is then introduced from a conventional fluid source into the hollow interior of cannula 22 and accordingly through the passageway 30 in the pin 26 and into the hollow chamber 44 of balloon 38. Sufficient fluid is introduced to partially expand the balloon and facilitate its natural flotation as it is directed by the flowing blood, for example, in the vessel to the desired location.

When the desired location is reached, as shown in FIG. 3, further fluid from the fluid source is introduced preferably under pressure as before through the catheter assembly to further expand balloon 38 until the balloon seals against the inner wall 54 of vessel 50.

When a satisfactory seal has occurred, detachment is then initiated in the manner depicted in FIG. 4. Further fluid from the fluid source is introduced through the cannula and the pin and back pressure forces the fluid to exit through side opening 32 in the pin into small chamber 48. Expansion of the balloon portion surrounding small chamber 48 causes the mouth portion 40 of the balloon to expand and detach from frictional engagement with expanded end portion 28 of the cannula. This permits the cannula and frictionally held pin to withdraw from the balloon 38. Materials are chosen so that the frictional engagement between the cannula and the pin is greater than the frictional engagement between the self-sealing plug 34 and the pin. Thus the pin will withdraw from plug 34 and will detach with the cannula from the balloon 38. Naturally the balloon engagement with the interior wall 54 of the vessel will retain the balloon in position while the cannula 22 and pin 26 are withdrawn therefrom. The arrow in FIG. 4 shows the direction of withdrawal of the cannula and connected pin.

As pin 26 is withdrawn from self-sealing member 34, the self-sealing member 34 in cooperation with the surrounding elastomeric string 46 will close and seal the open end of balloon 38 in expanded condition with the fluid 51 therein, as shown in FIG. 5. The nature of the balloon filler fluid is such that with a semi-permeable membrane formed of a material such as Silastic rubber for the balloon, extra cellular fluid bathing the balloon, does not accummulate within the balloon because there is no significant osmotic gradient. The chosen fluid provides adequate opacification and prolonged occlusion is possible, particularly if the balloons are not overinflated at the time of embolization. The result is an effective vessel occlusion with the use of a detachable balloon, as shown in FIG. 6.

Successful examples of the above procedure were carried out with a number of catheter assemblies of the above discussed type. Under local anesthesia via left carotid artery cut-down and catherization, balloons were detached into the hepatic, gastrosplenic, renal, internal iliac and profunda femoral arteries. Uninflated balloons 1 mm in outside diameter (0.040 inches) were mounted on a 0.6 mm (0.023 inches) polyurethane catheter and introduced through a five French polyethylene catheter. The balloon catheter was injected through the introducing catheter after coiling the former in a fifty ml. syringe filled with flushing solution. Once the balloon catheter emerged from the introducing catheter slight distention of the balloon with radiopaque contrast media allowed flow direction of the balloon to the final site of emobilization.

In a number of balloon catheters introduced in the above manner, a radiopaque contrast media of 60 percent sodium-meglumine diatrozoate (R-60) in the amount of 0.15 to 0.2 ml. was utilized to render the balloons radiopaque. In a further selected number of balloons, R-60 was diluted to a 30 percent iodine concentration (R-30) with the addition of sterile water. Following balloon detachment in the above described manner, post-occlusion angiography was performed via the introducing catheter. The results were observed by serial radiographs obtained over an extended period to demonstrate that, among other factors, that the osmolarity of the distending contrast media is an important variable influencing the permanency of Silastic rubber balloon occlusion.

Sodium-meglumate diatrozoate, in the concentrations utilized, has osmolarities of 1511 and 680 mOsm/l, which are significantly higher than blood (270–290 mOsm/l). Silastic rubber appeared to behave like any semi-permeable membrane. Extra cellular bathing the balloon crossed the Silastic rubber membrane thereby reducing the osmotic gradient. These effects were much less apparent with R-30 than with R-60 solutions. The tests also show that care should be taken not to overinflate the balloons at the time of embolization. The results show that prolonged occlusion is possible with the technique as described above.

It is suggested that contrast agents be employed with osmolarities near that of blood. With this in mind, another effective contrast agent is Cholografin Meglumine manufactured by Squibb, Inc., of Princeton, N.J. 08540. The undiluted 52 percent Ioditamide Meglumine solution has an iodine concentration of 260 mg. of iodine/ml and an osmolarity of 630 milliosmoles/liter. This means that this material can be diluted by one-third and achieve the same radiopacity as Metrizamide at an osmolarity which is just slightly over that of blood. A series of in vitro measurements of changes in osmolarity were made after using dilute Cholografin with balloons of the above type, showing essentially no change in osmolarity five days after the balloons were placed in saline.

In summary, slicone behaves like a semi-permeable membrane and permanency of detachable balloon inflation is dependent on the osmolarity of the filling substance within the volume limits of detachable balloons. Detachable balloons filled with hyperosmotic contrast agents swell and lose radiopacity. In testing with two contrast agents, one of 1500 millisomoles/liter and the other with 691 milliosmoles/liter resulted in confirmation in vivo that balloon swelling occurred and there was decreased radiopacification on serial radiographs. It was also determined that balloons filled with the hypoersmotic contrast agents would rupture before those filled with less osmotically active radio opaque filler.

Further confirmation of the importance of osmolarity was determined by using Metrizamide, an iso-osmotic contrast agent. None of the experiments employing the Metrizamide balloons ruptured after five months of observation. Testing also confirmed in vitro that silicone is a semi-permeable membrane. This was accomplished by placing balloons filled with contrast agents of different osmolarity in saline and measuring percent changes of 12 hours, 36 hours and 5 days. This confirmed conclusively in vitro that the osmolarities fell in the balloons filled with hyperosmotic contrast agents. Thus, there was transfer of fluid across the semi-permeable membrane which would account for early rupture of balloons. It was also observed that balloons filled with hyperosmotic contrast agents would increase in size.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

What is claimed is:

1. A therapeutic medical procedure utilizing a miniature balloon catheter of the type including a resilient cannula adapted for attachment to a source of fluid and having a small outer diameter for insertion into small vessels containing fluid and an inflatable balloon having a mouth at the proximal end thereof detachably mounted on the end of the cannula in fluid communication therewith and sealing means provided to close the mouth of the balloon when the cannula is detached therefrom, the therapeutic medical procedure comprising; inserting the balloon catheter into a small vessel, permitting the catheter to advance to a desired location in the vessel, attaching the balloon catheter to a source of fluid having an osmolarity substantially the same as the fluid in the vessel and being a contrast agent and inflating the balloon to the volume limits of the balloon with fluid from the fluid source through the cannula until the balloon is fixed in position in the vessel, and detaching the cannula from the balloon and removing the cannula from the vessel with the sealing means sealing the mouth of the inflated balloon and the fluid therein maintaining the balloon in inflated position for an extended period of time to create a vessel occlusion.

2. The invention in accordance with claim 1, wherein the fluid from the fluid source is radiopaque and the balloon is formed of a semi-permeable material.

3. The invention in accordance with claim 2, wherein the balloon is formed of silicone material thereby permitting it to act as a semi-permeable membrane.

4. The invention in accordance with claim 1, wherein the fluid from the fluid source is a Cholografin-Iodipamide Meglumine solution.

5. The invention in accordance with claim 1, wherein the fluid from the fluid source is a metrizamide solution.

6. The invention in accordance with claim 1, wherein the fluid from the fluid source is a Renografin-30 solution.

7. The invention in accordance with claim 1, wherein after insertion of the balloon catheter into the small vessel, a predetermined amount of fluid is introduced through the cannula into the balloon to partially inflate the balloon and permit the balloon portion and attached cannula to be directed by the fluid flow within the vessel to the desired location.

8. The invention in accordance with claim 1, wherein the fluid is introduced through the cannula into the balloon under pressure.

9. The invention in accordance with claim 1, wherein the balloon is detected from the cannula through the use of detachment means responsive to fluid introduced beyond the amount of fluid required to expand the balloon to the desired amount to fix it in position in the vessel so that the further fluid expands the portion of the balloon mounted on the cannula to release the cannula and permit the cannula to be withdrawn from the balloon.

10. The invention in accordance with claim 9, wherein the sealing means is located at the location of the mouth of the balloon so that when the cannula is removed from the balloon the sealing means will be actuated to close the mouth of the balloon and seal the balloon with the fluid located therein.

11. The invention in accordance with claim 1 wherein the small vessel is a blood vessel.

12. The invention in accordance with claim 1 wherein the osmolarity of the fluid is approximately 290 mOsm/l.

13. The invention in accordance with claim 1 wherein the balloon has an outside diameter of approximately 1 mm when in uninflated condition.

14. A therapeutic medical procedure utilizing a miniature balloon catheter of the type including a resilient cannula adapted for attachment to a source of fluid and having an outer diameter of approximately 1 mm when uninflated for insertion into small blood vessels containing blood and an inflatable balloon formed of silicone material thereby permitting it to act as a semi-permeable membrane and having a mouth at the proximal end thereof detachably mounted on the end of the cannula in fluid communication therewith and sealing means provided to close the mouth of the balloon when the cannula is detached therefrom, the therapeutic medical procedure comprising; inserting the balloon catheter into a small blood vessel, attaching the balloon catheter to a source or radiopaque fluid of Cholografin-Iodipamide Meglumine solution having an osmolarity substantially the same as blood, introducing under pressure a predetermined amount of radiopaque fluid through the cannula into the balloon to partially inflate the balloon and permit the balloon portion and attached cannula to be directed by the blood flow within the vessel to the desired location, inflating the balloon to the volume limits of the balloon with radiopaque fluid from the fluid source through the cannula until the balloon is fixed in position in the vessel, and detaching the cannula from the balloon through the use of detachment means responsive to radiopaque fluid introduced under pressure beyond the amount of radiopaque fluid required to expand the balloon to the desired amount to fix it in position in the blood vessel so that the further radiopaque fluid expands the portion of the balloon mounted on the cannula to release the cannula and permit the cannula to be withdrawn from the balloon with the sealing means sealing the mouth of the inflated balloon and the radiopaque fluid therein maintaining the balloon in inflated position for an extended period of time to create a vessel occlusion.

15. A therapeutic medical procedure utilizing a miniature balloon catheter of the type including a resilient cannula adapted for attachment to a source of fluid and having an outer diameter of approximately 1 mm when uninflated for insertion into small blood vessels containing blood and an inflatable balloon formed of silicone material thereby permitting it to act as a semi-permeable membrane and having a mouth at the proximal end thereof detachably mounted on the end of the cannula in fluid communication therewith and sealing means provided to close the mouth of the balloon when the cannula is detached therefrom, the therapeutic medical procedure comprising; inserting the balloon catheter into a small blood vessel, attaching the balloon catheter to a source of radiopaque fluid of metrizamide solution having an osmolarity substantially the same as blood, introducing under pressure a determined amount of radiopaque fluid through the cannula into the balloon to partially inflate the balloon and permit the balloon portion and attached cannula to be directed by the blood flow within the vessel to the desired location, inflating the balloon to the volume limits of the balloon with radiopaque fluid from the fluid source through the cannula until the balloon is fixed in position in the vessel, and detaching the cannula from the balloon through the use of detachment means responsive to radiopaque fluid introduced under pressure beyond the amount of radiopaque fluid required to expand the balloon to the desired amount to fix it in position in the blood vessel so that the further radiopaque fluid expands the portion of the balloon mounted on the cannula to release the cannula and permit the cannula to be withdrawn from the balloon with the sealing means sealing the mouth of the inflated balloon and the radiopaque fluid therein maintaining the balloon in inflated position for an extended period of time to create a vessel occlusion.

16. A therapeutic medical procedure utilizing a miniature balloon catheter of the type including a resilient cannula adapted for attachment to a source of fluid and having an outer diameter of approximately 1 mm when uninflated for insertion into small blood vessels containing blood and an inflatable balloon formed of silicone material thereby permitting it to act as a semi-permeable membrane and having a mouth at the proximal end thereof detachably mounted on the end of the cannula in fluid communication therewith and sealing means provided to close the mouth of the balloon when the cannula is detached therefrom, the therapeutic medical procedure comprising; inserting the balloon catheter into a small blood vessel, attaching the balloon catheter to a source of radiopaque fluid of Renografin-30 solution having an osmolarity substantially the same as blood, introducing under pressure a predetermined amount of radiopaque fluid through the cannula into the balloon to partially inflate the balloon and permit the balloon portion and attached cannula to be directed by the blood flow within the vessel to the desired location, inflating the balloon to the volume limits of the balloon with radiopaque fluid from the fluid source through the cannula until the balloon is fixed in position in the vessel, and detaching the cannula from the balloon through the use of detachment means responsive to radiopaque fluid introduced under pressure beyond the amount of radiopaque fluid required to expand the balloon to the desired amount to fix it in position in the blood vessel so that the further radiopaque fluid expands the portion of the balloon mounted on the cannula to release the cannula and permit the cannula to be withdrawn from the balloon with the sealing means sealing the mouth of the inflated balloon and the radiopaque fluid therein maintaining the balloon in inflated position for an extended period of time to create a vessel occlusion.

17. A balloon-catheter assembly for use in a medical procedure which produces embolization of a fluid-containing vessel comprising:
   a resilient cannula having a proximal portion adapted for connection to a source of external fluid, said cannula having an outer diameter adapted for insertion into said fluid-containing vessel;
   an inflatable balloon member detachably connected by a fluid-tight sealing arrangement to a distal portion of said cannula, the interior of said balloon being in fluid communication with said cannula for the reception of external fluid from said source therein when said cannula is connected thereto for inflating said balloon member inside said vessel, said balloon member including an inflatable portion made of an expandable semi-permeable material;

said balloon member inside said vessel adapted to be inflated by a sufficient quantity of external fluid to cause embolization of said vessel, and the external fluid therein having its osmolarity property substantially the same as the osmolarity of the fluid in the vessel and being a contrast agent; and said balloon member adapted to remain inflated for long-term embolization of said vessel subsequent to detachment inside said vessel.

18. The assembly of claim 17 wherein said semi-permeable material is silicone rubber.

19. The assembly of claim 17 wherein said external fluid has an osmolarity property substantially the same as the osmolarity of blood.

20. The assembly of claim 19 wherein the osmolarity of said external fluid is in the range of about 270 to 290 mOsm/l.

21. The assembly of claim 17 wherein said external fluid is an iso-osmotic contrast agent.

22. The assembly of claim 21 wherein said contrast agent is Metrizamide.

23. The assembly of claim 17 wherein said external fluid is radiopaque.

24. The assembly of claim 23 wherein said radiopaque fluid is a Cholografin-Iodipamide Meglumine solution having an osmolarity property substantially the same as the osmolarity of blood.

25. The assembly of claim 23 wherein said radiopaque fluid is a Renografin-30 solution having an osmolarity property substantially the same as the osmolarity of blood.

26. An inflated balloon device implanted in a fluid-containing vessel and producing an embolization thereof comprising:

a fluid-tight balloon member of semi-permeable material expanded against the walls of said fluid-containing vessel in fixed engagement therewith; and a fluid sealed inside said balloon member in sufficient quantity to effectuate the expansion of said balloon member, said expansion fluid having an osmolarity property substantially the same as the osmolarity of the fluid in the vessel and being a contrast agent.

27. The assembly of claim 26 wherein said semi-permeable material is silicone rubber.

28. The assembly of claim 26 wherein said expansion fluid has an osmolarity property substantially the same as the osmolarity of blood.

29. An inflated balloon device implanted in a blood vessel and producing an embolization thereof comprising:

a fluid-tight balloon member of semi-permeable material expanded against the walls of said blood vessel in fixed engagement therewith; and a fluid sealed inside said balloon member in sufficient quantity to effectuate the expansion of said balloon member, said expansion fluid having an osmolarity property substantially the same as the osmolarity of blood and being a contrast agent.

30. A balloon catheter comprising; a resilient cannula adapted for attachment to a first fluid source and insertable into a vessel containing a second fluid, an inflatable balloon detachably mounted on the end of the cannula in fluid communication therewith, said balloon having been inflated by first fluid sufficient to fix the balloon in position in the vessel with the first fluid having an osmolarity substantially the same as the second fluid in the vessel and being a contrast agent, detachment means to separate the balloon from the cannula after the balloon has been inflated and fixed in position in the vessel, and sealing means to seal the inflated balloon after the cannula is detached to retain the balloon in inflated condition in the vessel for an extended period of time to create a vessel occlusion.

31. An inflatable balloon adapted to be inserted in a fluid containing vessel to create a vessel occlusion for an extended period of time comprising a balloon member having a sealable opening therein a second fluid having been introduced through the sealable opening to inflate the balloon and fix the balloon in position in a vessel whereupon sealing of the sealable opening in the balloon retains the balloon in inflated condition in the vessel, and the second fluid in the balloon having an osmolarity substantially the same as the fluid in the vessel and being a contrast agent to create a vessel occlusion for an extended period of time.

* * * * *